(12) United States Patent
Francischelli et al.

(10) Patent No.: US 6,706,038 B2
(45) Date of Patent: Mar. 16, 2004

(54) SYSTEM AND METHOD FOR ASSESSING TRANSMURALITY OF ABLATION LESIONS

(75) Inventors: David E. Francischelli, Anoka, MN (US); Scott E. Jahns, Hudson, WI (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/409,871

(22) Filed: Apr. 9, 2003

(65) Prior Publication Data

US 2003/0195384 A1 Oct. 16, 2003

Related U.S. Application Data

(60) Division of application No. 09/844,220, filed on Apr. 26, 2001, now Pat. No. 6,584,360, which is a continuation-in-part of application No. 09/560,507, filed on Apr. 27, 2000, now abandoned.

(51) Int. Cl.[7] ................................................. A61F 7/00
(52) U.S. Cl. ........................... 606/34; 606/41; 607/98; 607/115; 607/119; 128/898
(58) Field of Search ......................... 606/34, 41, 45–47, 606/50; 607/98, 115, 116, 119; 128/898

(56) References Cited

U.S. PATENT DOCUMENTS

| | | | |
|---|---|---|---|
| 3,951,133 A | 4/1976 | Reese | 128/2 |
| 4,064,872 A | 12/1977 | Caplan | 128/2 |
| 4,378,808 A | 4/1983 | Lichtenstein | 128/736 |
| 4,414,984 A | 11/1983 | Zarudiansky | 128/774 |
| 4,450,843 A | 5/1984 | Barney et al. | 128/690 |
| 4,682,605 A | 7/1987 | Hoffman | 128/736 |
| 5,233,515 A | 8/1993 | Cosman | 364/413 |
| 5,423,808 A | 6/1995 | Edwards et al. | 606/34 |
| 5,443,463 A | 8/1995 | Stern et al. | 606/51 |
| 5,456,682 A | 10/1995 | Edwards et al. | 606/31 |
| 5,496,342 A | 3/1996 | Urich | 606/169 |
| 5,573,533 A | 11/1996 | Strul | 606/34 |
| 5,584,830 A | 12/1996 | Ladd et al. | 606/34 |
| 5,596,995 A | 1/1997 | Sherman et al. | 128/736 |
| 5,647,868 A | 7/1997 | Chinn | 606/21 |
| 5,688,266 A | 11/1997 | Edwards et al. | 606/31 |
| 5,688,267 A | 11/1997 | Panescu et al. | 606/41 |
| 5,702,386 A | 12/1997 | Stern et al. | 606/34 |
| 5,707,369 A | 1/1998 | Vaitekunas et al. | 606/31 |
| 5,743,903 A | 4/1998 | Stern et al. | 606/31 |
| 5,755,715 A | 5/1998 | Stern et al. | 606/31 |
| 5,755,760 A | 5/1998 | Maguire et al. | 607/122 |
| 5,769,847 A | 6/1998 | Panescu et al. | 606/42 |
| 5,810,802 A | 9/1998 | Panescu et al. | 606/31 |
| 5,833,688 A | 11/1998 | Sieben et al. | 606/41 |
| 5,853,409 A | 12/1998 | Swanson et al. | 606/31 |
| 5,868,736 A | 2/1999 | Swanson et al. | 606/34 |
| 5,868,743 A | 2/1999 | Saul et al. | 606/49 |
| 5,897,552 A | 4/1999 | Edwards et al. | 606/31 |
| 5,906,614 A | 5/1999 | Stern et al. | 606/42 |
| 5,935,124 A | 8/1999 | Klumb et al. | 606/42 |
| 5,954,719 A | 9/1999 | Chen et al. | 606/42 |
| 5,957,961 A | 9/1999 | Maguire et al. | 607/99 |
| 5,971,980 A | 10/1999 | Sherman | 606/34 |
| 6,030,379 A | 2/2000 | Panescu et al. | 606/34 |
| 6,042,580 A | 3/2000 | Simpson | 606/32 |
| 6,045,550 A | 4/2000 | Simpson et al. | 606/42 |
| 6,053,912 A | 4/2000 | Panescu et al. | 606/40 |
| 6,056,745 A | 5/2000 | Panescu et al. | 606/42 |
| 6,063,078 A | 5/2000 | Wittkampf | 606/41 |

(List continued on next page.)

*Primary Examiner*—Rosiland K. Rollins
(74) *Attorney, Agent, or Firm*—Thomas G. Berry; Daniel W. Latham

(57) ABSTRACT

A device for monitoring temperature generated by an ablation apparatus on organic tissue is provided. The device comprises a temperature sensing pad; and an output device to receive and display a representation of a lesion found on the ablated organic tissue. Ablation systems incorporating the device and methods of using the device are also provided.

2 Claims, 10 Drawing Sheets

U.S. PATENT DOCUMENTS

| | | | |
|---|---|---|---|
| 6,096,035 A | 8/2000 | Sodhi et al. | 606/41 |
| 6,113,591 A | 9/2000 | Whayne et al. | 606/34 |
| 6,135,968 A | 10/2000 | Brounstein | 600/549 |
| 6,161,543 A | 12/2000 | Cox et al. | 128/898 |
| 6,162,184 A | 12/2000 | Swanson et al. | 600/549 |
| 6,197,021 B1 | 3/2001 | Panescu et al. | 606/31 |
| 6,217,573 B1 | 4/2001 | Webster | 606/41 |
| 6,217,574 B1 | 4/2001 | Webster | 606/41 |
| 6,237,605 B1 | 5/2001 | Vaska et al. | 128/898 |
| 6,293,943 B1 | 9/2001 | Panescu et al. | 606/41 |
| 6,312,425 B1 | 11/2001 | Simpson et al. | 606/32 |
| 6,322,558 B1 | 11/2001 | Taylor et al. | 606/34 |
| 6,356,790 B1 | 3/2002 | Maguire et al. | 607/102 |
| 6,383,144 B1 | 5/2002 | Mooney et al. | 600/549 |
| 6,425,894 B1 | 7/2002 | Brucker et al. | 606/41 |
| 6,440,129 B1 | 8/2002 | Simpson | 606/42 |
| 6,451,011 B2 | 9/2002 | Tu | 606/21 |

60 bottom view

60

SYSTEM AND METHOD FOR ASSESSING TRANSMURALITY OF ABLATION LESIONS

CROSS-REFERENCE TO RELATED APPLICATION

The present application is a divisional of U.S. Ser. No. 09/844,220 filed on Apr. 26, 2001 now U.S. Pat. No. 6,584,360, which is a continuation-in-part of U.S. Ser. No. 09/560,507, filed Apr. 27, 2001 now abandoned.

FIELD OF THE INVENTION

This invention relates to ablation devices that are used to create lesions in tissue. More particularly, this invention relates to ablation devices that use temperature-sensing elements to monitor the transmurality of the lesions.

BACKGROUND OF THE INVENTION

The action of the heart is known to depend on electrical signals within the heart tissue. Occasionally, these electrical signals do not function properly. The maze procedure is a surgical operation for patients with atrial fibrillation that is resistant to medical treatment. In this procedure, incisions are created in the right and left atria to produce an orderly passage of the electrical impulse from the SA node to the atrioventricular node. Blind passageways are also created to suppress reentry cycles. Currently, the lesions may still be created using a traditional cut and sew technique. The scar tissue resulting from the procedure results in a non-conductive lesion.

Ablation of cardiac conduction pathways in the region of tissue where the signals are malfunctioning is now being used to replace the surgical incisions. Ablation is also used therapeutically with other organ tissue, such as the lungs, liver, prostate and uterus. Ablation may also be used in treatment of disorders such as tumors, cancers or undesirable growth.

Currently, electrophysiology (EP) ablation devices generally have one or more electrodes at their tips. These may be used for both diagnosis and therapy. In one instance, electrodes at the tips of EP ablation devices allow the physician to measure electrical signals along the surface of the heart. This is called mapping. When necessary, in another instance, the physician can also ablate certain tissues using, typically, radio frequency (RF) energy conducted to one or more ablation electrodes.

Sometimes ablation is necessary only at discrete positions along the tissue. This is the case, for example, when ablating accessory pathways, such as in Wolff-Parkinson-White syndrome or AV nodal reentrant tachycardias. At other times, however, ablation is desired along a line, called linear ablation. This is the case for atrial fibrillation, where the aim is to reduce the total mass of contiguous (electrically connected) atrial tissue below a threshold believed to be critical for sustaining multiple reentrant wavelets. Linear lesions are created between electrically non-conductive anatomic landmarks to reduce the contiguous atrial mass.

Linear ablation is currently accomplished in one of several ways. One way is to position the tip portion of the ablation device so that an ablation electrode is located at one end of the target site. This may be done, for example, with an electrode positioned on a "pen-like" device. Then energy is applied to the electrode to ablate the tissue adjacent to the electrode. The tip portion of the electrode is then slid along the tissue to a new position and then the ablation process is repeated. This is sometimes referred to as the "spot burn" technique. This technique is time-consuming (which is not good for the patient) and requires multiple accurate placements of the electrode (which may be difficult for the physician). Furthermore, even if the ablation process creates a continuously linear line along the top surface of the target tissue, it is not assured that the tissue is continuously and completely ablated through further layers of the target tissue (i.e. it is not assured that transmurality is achieved.) Transmurality is achieved when the full thickness of the target tissue is ablated.

A second way of accomplishing linear ablation is to use an ablation device having a series of spaced-apart band or coil electrodes which, after the electrode portion of the ablation device has been properly positioned, are energized simultaneously or one at a time to create the desired lesion. If the electrodes are close enough together the lesions run together sufficiently to create a continuous linear lesion. While this technique eliminates some of the problems associated with the "spot burn" technique, some repositioning of the ablation device may be required to create an adequately long lesion. In addition, it may be difficult to obtain adequate tissue contact pressure for each electrode in a multi-electrode ablation device. Also, the use of multiple electrodes to create the linear lesion tends to make the tip portion more expensive to make, more bulky and may cause the tip portion to be stiffer than is possible when a single, or very few, electrodes are used. The added complications resulting from the use of multiple ablation electrodes can also reduce overall reliability.

Ablation devices typically include a conductive tip, which serves as one electrode in an electrical circuit. The electrical circuit is completed via a grounding electrode that may also be on the device or may be coupled to the patient. By controlling the level of energy transmitted to the ablation electrode, the user is able to control the amount of heat generated. The ablation site may also be irrigated to cool the electrode and create greater lesion depth.

In order to control the level of energy transmitted, the user must monitor the level of energy being transmitted from the electrode. Typical systems for monitoring ablation energy rely on a thermocouple element located within the ablation device, generally near the electrode. This temperature-measuring element effectively measures the temperature of the electrode rather than the tissue being ablated. Particularly when the site is being irrigated with a conductive fluid, the temperature of the tissue may differ to some degree from the temperature of the ablation device.

Another concern with the ablation approaches is the difficulty of assessing when the lesion is transmural, that is, assessing that the lesion penetrates across the full thickness of the atrial tissue. Physicians have generally relied on their best judgment or historical data to predict when a lesion is fully transmural. Currently, there is no assessment of lesion transmurality. A physician simply creates a lesion by applying energy for a pre-determined length of time over a specific length (i.e. 30 W for 30 seconds over a length of 1 cm). This combination has been determined by exhaustive bench and animal experiments. Nonetheless, the human factor can result in moving the device too quickly, or changes in tissue thickness can require additional energy. If a lesion is incomplete, it may not be effective in controlling the arrhythmia, and may even be pro-arrhythmic.

It would thus be desirable to have an ablation device which, when positioned, is capable of easily and thoroughly creating a transmural lesion. It would further be desirable to have an ablation device that provides feedback that a lesion is complete and transmural. It would further be desirable to have a system for assessing the transmurality of lesions created by ablation, particularly to provide feedback to the user on the condition of the lesion while the ablation is taking place.

SUMMARY OF THE INVENTION

One aspect of the invention provides a sensor which monitors tissue temperature generated by an ablation apparatus on organic tissue. The sensor includes a temperature-sensing pad and an output device in communication with the pad. The output device receives and displays a representation of a lesion found on the ablated organic tissue. The temperature-sensing pad may incorporate temperature-sensing elements such as, for example, thermocouples, thermisters, temperature-sensing liquid crystals, or temperature-sensing chemicals. The temperature-sensing pad may be mounted on a glove, or may otherwise be adapted to fit over a user's finger. The temperature-sensing pad may be mounted on a handle or stick, or other maneuvering mechanism or means for placing or positioning the pad against tissue. The apparatus may also include a conductive element. The output device of the sensor may be a visual display on a monitor or a visual display on the pad itself.

Another aspect of the present invention provides a system for assessing transmurality of an ablation in a tissue. The system includes an ablation apparatus which is used to ablate the front side of the tissue, a temperature-sensing pad which is placed against the back side of the tissue and senses temperature changes along the back side of the tissue. The system also includes an output device in communication with the pad that may indicate the temperature of the tissue. The system may also include temperature-sensing elements incorporated into the temperature-sensing pad.

Another aspect of the invention provides a method of ablating organic tissue. A sensor that senses the temperature of the tissue to be ablated is provided. The sensor is positioned against a back side of the tissue. The tissue is ablated with an ablation apparatus against the front side of the tissue. The pad senses the temperature changes as the tissue is ablated. The tissue may then be ablated in accordance with the temperature changes. The temperature of the tissue may be indicated using an output device.

Another aspect of the invention provides a device for monitoring temperature generated by an ablation apparatus on organic tissue. The device includes a temperature-sensing pad incorporating a plurality of temperature-sensing liquid crystals and an output device in communication with the pad that receives and displays a representation of a lesion found on the organic tissue. This pad may be used in conjunction with a color scheme in which each color indicates a temperature.

Another aspect of the invention provides a device for monitoring temperature generated by an ablation apparatus on organic tissue. The device includes a finger pad with plurality of temperature-sensing elements incorporated therein. The finger pad is operatively adapted to fit over a finger. The device also includes an output device in communication with the finger pad that is adapted to receive and display a representation of a lesion found on the organic tissue. The finger pad may also indicate the temperature generated by the ablation apparatus.

Another aspect of the invention provides a system for assessing transmurality of an ablation in a tissue. The system includes an ablation apparatus that is adapted to ablate a front face of the tissue and a temperature-sensing pad that incorporates a conductive element and senses temperature along a back side of the tissue. The system also includes an output device in communication with a pad which indicates the temperature of the tissue. The temperature pad may also be the conductive element.

The foregoing and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
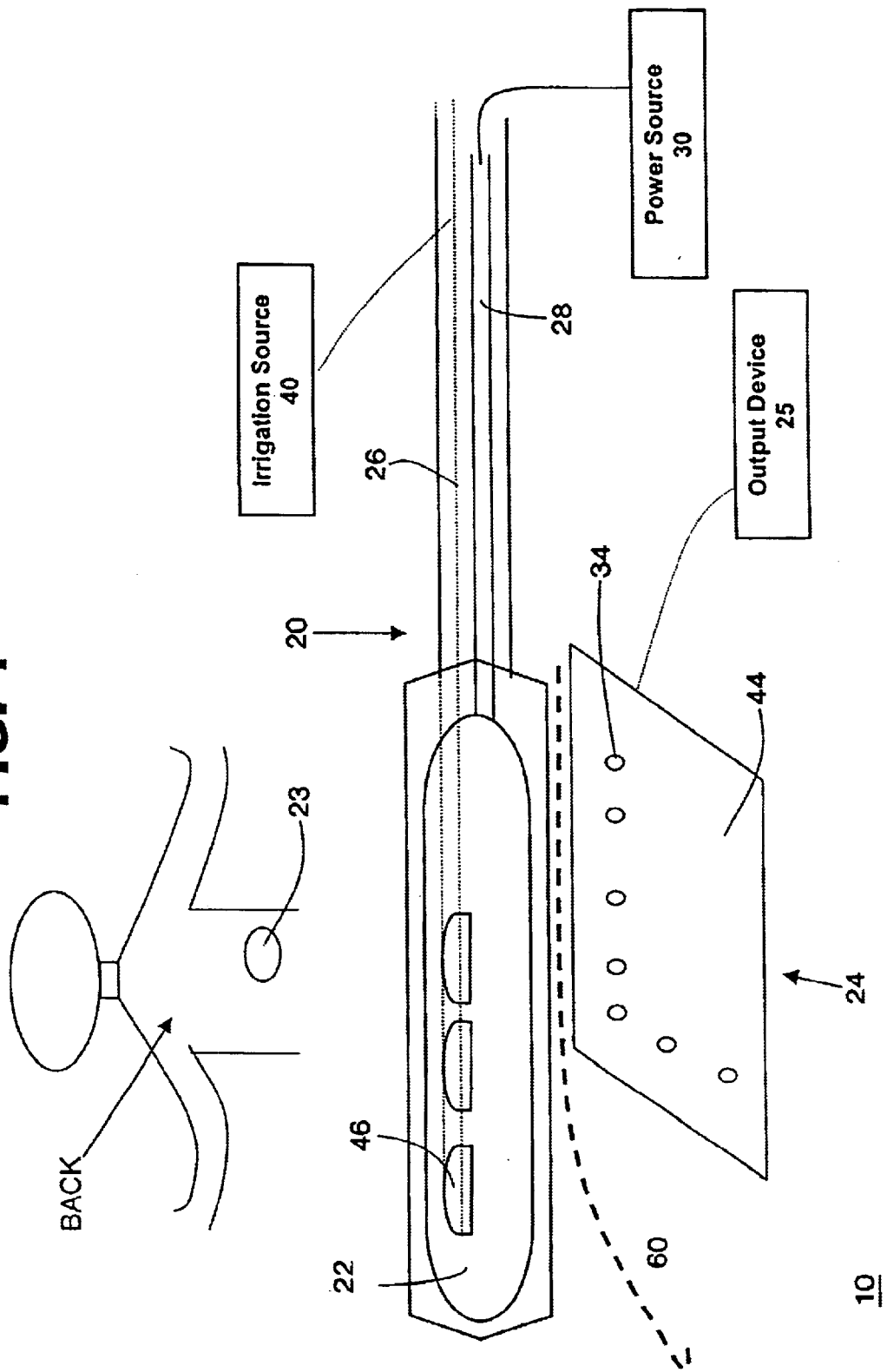
FIG. 1 illustrates a schematic view of one embodiment of a system for ablating tissue in accordance with the present invention.

FIG. 1 shows a schematic view of a system 10 for ablating tissue in accordance with the present invention. Typically the tissue to be ablated will be located within the body cavity, such as the endocardial or epicardial tissue of the heart. Other body organ tissue, such as the liver or lungs, can also be ablated using the present invention. System 10 may also be used in any location where it is necessary to measure tissue temperature, such as during ventricular ablation. System 10 may include an ablation device 20 that comprises at least one conductive electrode 22, and a connection 28 to a source of ablation energy. System 10 may further include a power source 30 that provides ablation energy. System 10 may further include a sensor 24 that may be used to measure the energy being transmitted through the electrode 22 to the target tissue 60. System 10 also may include an irrigation source 40 that provides irrigation fluid to the ablation site. Ablation device 20 or electrode 22 of ablation device 20 may also include fluid openings 46 through which irrigation fluid may flow to the site via fluid conduit 26. System 10 may also include an indifferent (or non-ablating) electrode 23 which may serve as the return plate for energy transmitted through electrode 22.

Ablation device 20 may be any suitable ablation tool such as, for example, a catheter, an electrocautery device, an electrosurgical device, a suction-assisted ablation tool, an ablation pod, an ablation paddle, an ablation hemostat or an ablation wire. Ablation device 20 and its components are preferably made of a biocompatible material such as stainless steel, biocompatible epoxy or biocompatible plastic. Preferably, a biocompatible material prompts little allergenic response from the patient's body and is resistant to corrosion from being placed within the patient's body. Furthermore, the biocompatible material preferably does not cause any additional stress to the patient's body, for example, it does not scrape detrimentally against any elements within the surgical cavity.

Preferably, ablation device 20 may be permanently or removably attached to or incorporate a maneuvering apparatus for manipulating device 20 onto a tissue surface. Such an apparatus may be, for example, a pen-like maneuvering handle 12. Electrodes of ablation device 20 may also be located on one or more jaws of a hemostat-like device. As seen in FIG. 1, ablation device 20 may also be used in conjunction with a traditional catheter, for example, in a closed heart ablation procedure. Ablation device 20 may also be maneuvered with a leash or pull-wire assembly. Alternatively any appropriate flexible or rigid handle may be used as a maneuvering apparatus. Alternatively, any appropriate endoscopic or thoroscopic maneuvering apparatus may also be used with device 20.

Device 20 also preferably includes a connection 28 suitable for conducting energy to device 20, particularly to conductive element 22 from a power source.

The conductive element 22 of ablation device 20 is preferably an electrode. This electrode 22 may be positioned in any suitable place on device 20. Preferably electrode 22 is placed near an end of the device 20, away from the user, to be more easily manipulated against the tissue 60 to be ablated. Electrode 22 may be, for example, a weeping electrode, a double wound coil electrode, an electrode needle or any other suitable electrode.

System 10 also includes sensor 24. Sensor 24 may comprise one or more temperature-sensing elements 34 placed on or integrated into a support surface 44. Temperature-sensing elements may be, for example, thermocouples or thermisters. Preferably, elements 34 are arranged in a grid on support surface 44. Preferably, elements 34 are arranged in close proximity to each other. Support surface 44 may be a rigid material such as, for example, Plexiglas™. Support surface 44 may also be a flexible material such as, for example, biocompatible rubber or plastic. Alternatively, support surface 44 may be made of any material that may appropriately incorporate temperature-sensing elements 34. Sensor 24 may be powered by any suitable power source. Connection 28 described above may provide power to sensor 24 from power source 30. Sensor 24 may also have its own connection and/or its own power source.

System 10 may also include an electrode 23 which may serve as the return plate for energy transmitted through electrode 22. Electrode 23 may be, for example, a weeping electrode, a double wound coil electrodes, an electrode needles or any other suitable electrode. An electrically conductive element incorporated into sensor 24 may serve as the electrode 23. Alternatively sensor 24 may be electrically conductive and serve as electrode 23. Electrodes 22, 23 may act as anode and cathode to each other, completing a bipolar system. If electrodes 22 and 23 are close to each other, the electric current has less area to cross. This is beneficial because the current is less likely to cross into undesired areas (for example, tissue other than target tissue). Such a bipolar system is also known to create narrower and deeper lesions. Incorporation of electrode 23 into sensor 24 may facilitate such a bipolar system.

Figure 2:
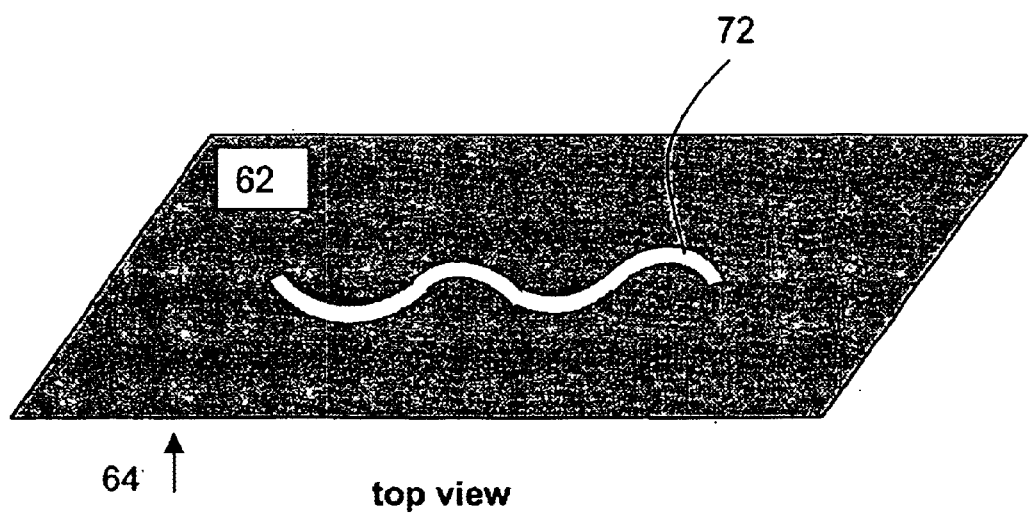
FIG. 2 illustrates a top view of a typical ablation lesion in a target tissue surface.

FIG. 2 shows a target tissue surface 60. Typically target tissue may have two surfaces 62, 64. Front surface 62 is the surface that may contact the ablation device 20. Back surface 64 is the surface that may contact sensor 24. Preferably, support surface 44 is made of a material that may conform to surface 64 of the target tissue. In use, a user manipulates ablation device 20 so that electrode 22 contacts the surface 62 of the tissue to be ablated. Power source 30 provides energy to the device 20 via connection 28. This connection may be any suitable connection for conducting energy from power source 30 to device 20. Power source 30 may be any suitable power source such as, for example, standard electrical power available in the operating room. Once power source 30 is turned on, the user uses device 20 to ablate the tissue surface 62 with energy from the energized electrode 22. A top view of the lesion resulting from this ablation process is shown at 72. Lesion 72 is a continuous lesion.

Figure 3:
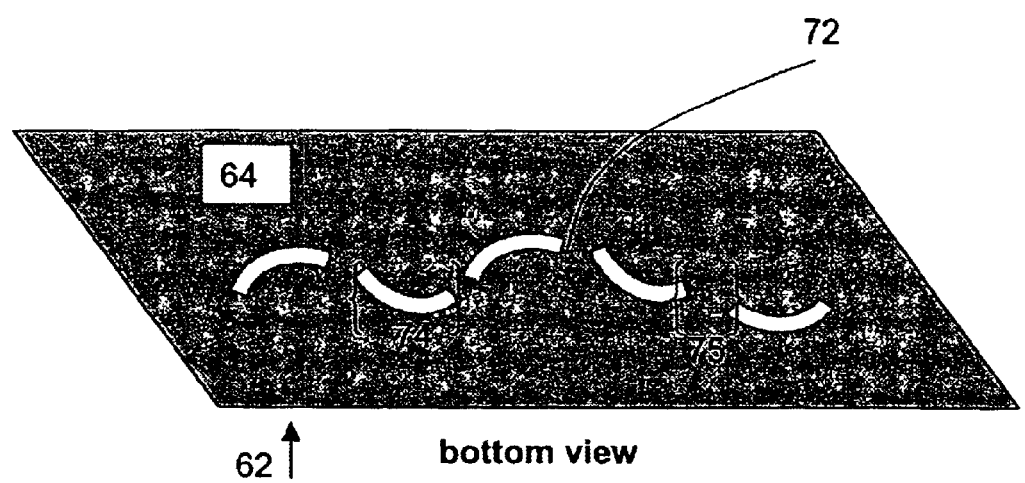
FIG. 3 illustrates a bottom view of a typical ablation lesion in a target tissue surface.

However as FIG. 3 shows, lesion 72 may not be continuous on back surface 64 of the tissue. Areas 74 of the lesion 72 are transmural to surface 64. However, areas 75 are not transmural. In areas 75, ablation has not penetrated through the complete thickness of the tissue. Because the tissue to be ablated is usually still within a body cavity, the user may only have visual access to front surface 62. The user may have difficulty accessing back surface 64 of the target tissue to assess transmurality. If lesion 72 is incomplete, i.e. is not transmural, it may not be effective in its intended purpose, such as for example, to control an arrhythmia. An incomplete lesion may even cause trauma to the patient.

Figure 4:
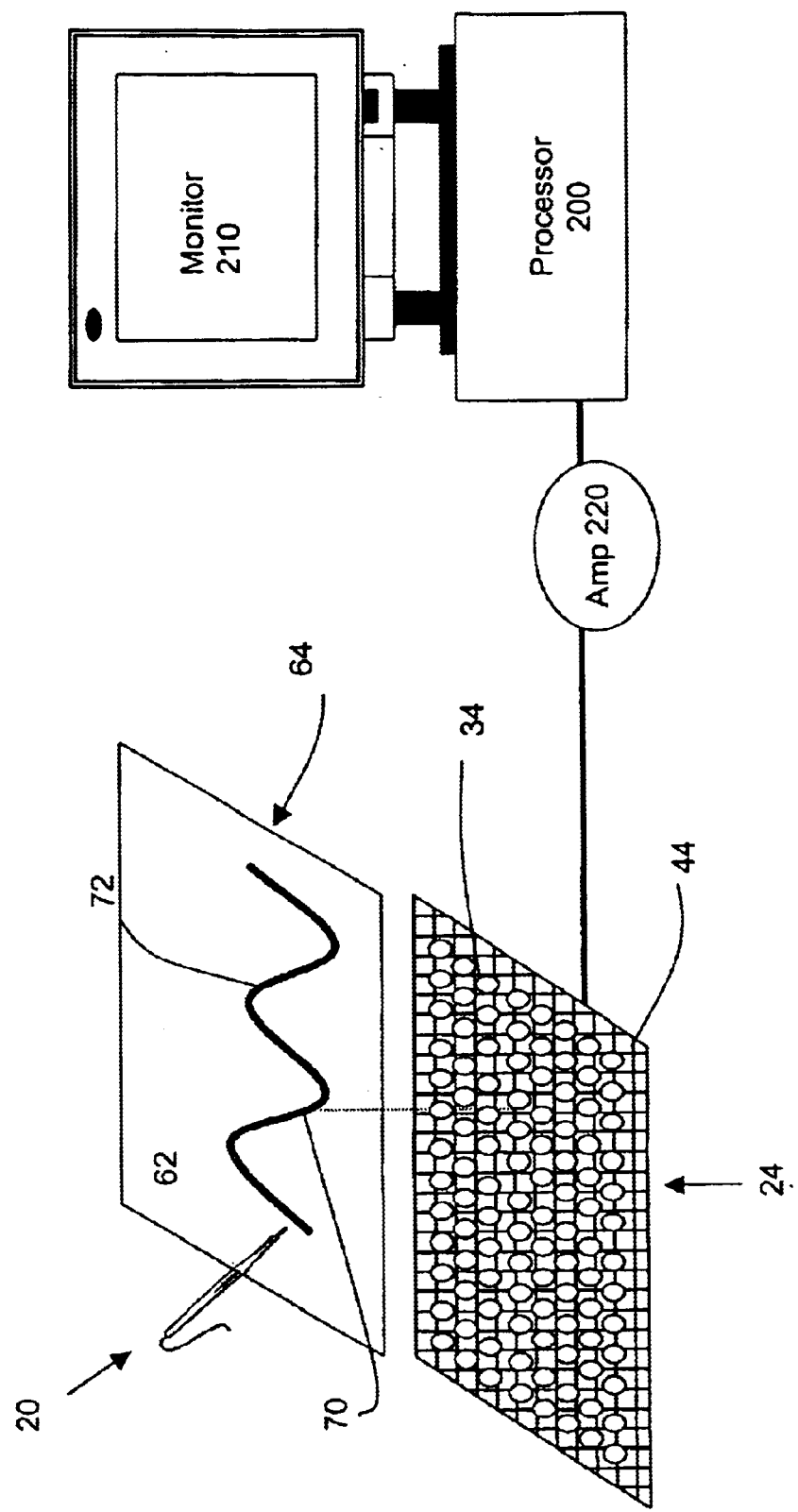
FIG. 4 illustrates another embodiment of a system for ablating tissue in accordance with the present invention.

A user may use the system 10 of the present invention to assess transmurality. In the embodiment shown in FIG. 4, the user places sensor 24 against back surface 64 of the target tissue. Sensor 24 may be any arrangement of temperature-sensing elements. Sensor 24 may be held in place against surface 64 using any appropriate holding apparatus. Sensor 24 may also be held in place manually. Sensor 24 may be attached, for example, using suction elements, clamps or suture material.

When positioned, each temperature-sensing element is in contact with an area of tissue (point of contact 70). As ablation occurs, each of the temperature-sensing elements 34 on support surface 44 senses the temperature of its point of contact 70. Each element creates a voltage corresponding to the temperature of the point of contact. Each element then transmits the voltage to a processor 200. Preferably the elements are arranged in close proximity to each other to better sense a continuous or nearly continuous area of tissue.

In one embodiment, the temperature of each point of contact 70 may be displayed, for example, on a LCD or CRT monitor 210. During ablation, the tissue will change in temperature. Ablation may be performed by heating the tissue to a suitable temperature. In one embodiment, the temperature increase at the point of contact may be sensed. Alternatively, ablation may be performed by freezing the tissue to a suitable temperature (such as −20° C to −40° C.). In another embodiment, the temperature decrease at the point of contact may be sensed. This temperature change may be shown on the monitor 210. By software control, the user may choose to display the information in a number of ways. The monitor 210 may show the current temperature of each point of contact 70. The monitor 210 may also lock and display the maximum temperature achieved at each point of contact 70. The monitor 210 may also indicate when each point of contact has reached an appropriate combination of temperature and time to ensure cell death. One such appropriate combination may be 60° C. for 5 seconds. Another combination may be 55° C. for 20 seconds. Another combination may be 50° C. for 15 seconds. Temperature information may be displayed to the user in any other suitable manner, such as for example, displaying a virtual representation of sensor 24 and ablation lesion 72 on the monitor 210.

The temperature combinations indicated above may indicate cell death. In order to achieve transmurality with device 20, the user may attempt to ablate from the area nearest to device 20 (surface 62) through the entire thickness of the target tissue to the area farthest from device 20 (surface 64). If the temperature of the surface farthest from device 20 (surface 64) is high enough to achieve cell death, the user may assume that the temperatures of the tissue nearer to device 20 are also high enough to achieve cell death. In such an instance, the user may assume that transmurality has been achieved. As described above, system 10 provides feedback on display 210 regarding the temperature of the surface 64 farthest from device 20 and thereby provides feedback on the transmurality of lesion 72.

The signal from sensor 24 may preferably be amplified by a suitable amplifier 220 before reaching processor 200. The amplifier may also be incorporated into processor 200. Alternatively, the amplifier may be a separate device.

In one embodiment, sensor 24 may be made of a rigid piece of material. The material may have a plurality of thermocouples attached in a grid configuration to its surface. In one embodiment of the invention, for example, fifteen thermocouples are glued in a 3×5 grid to a rigid piece of Plexiglas™. In this example, the thermocouples may be positioned approximately 2 to 3 mm apart from each other. The thermocouples are wired to a computer. Each thermocouple may be displayed as a dot or square on the monitor of the computer. Each of the thermocouple elements may contact a point on a target tissue. When the point on the target tissue reaches a certain temperature, the corresponding thermocouple element may send a signal to the computer. Preferably, the temperature-sensing elements may send constant signals to the computer. For example, the thermocouples may send a constant signal to the computer based on their voltage. As the temperature changes, the voltage of the thermocouples may change proportionately and the signal sent by the thermocouples may change proportionately. The corresponding dot or square on the monitor is then colored to indicate that a certain temperature has been reached. Alternatively, the corresponding dot or square may change color along with the temperature. For example, a dot may start out as blue when a thermocouple element first contacts the target tissue. Then the dot may turn yellow as the thermocouple element senses the tissue temperature to be 30° C. Finally the dot may turn red as the thermocouple element senses the tissue temperature to be 60° C.

Figure 5:
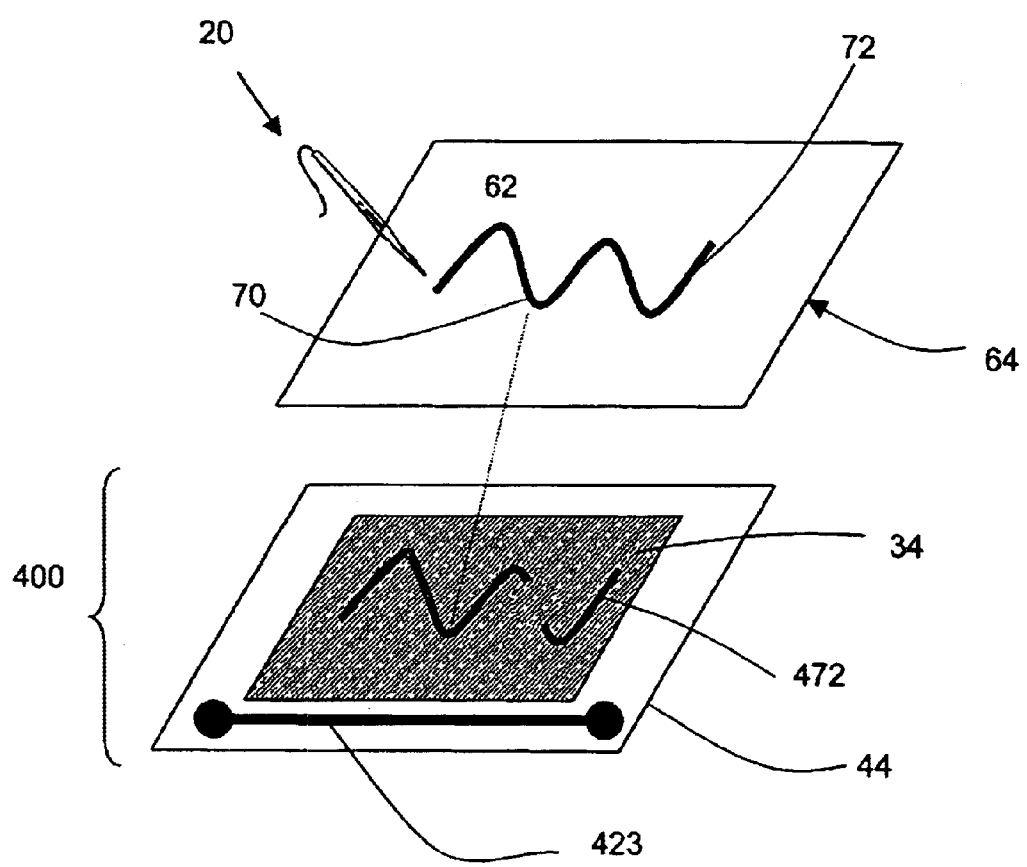
FIG. 5 illustrates another embodiment of a system for ablating tissue in accordance with the present invention.

In the embodiment shown in FIG. 5, sensor 24 may also be a disposable pad 400. Temperature-sensing elements 34 may be incorporated into this pad. These elements may be, for example, temperature-sensing liquid crystals or other chemical compounds such as those commonly used by medical professionals for disposable thermometer strips. Elements 34 may also be arranged in a grid configuration. Alternatively, elements 34 may be arranged so that they fill pad 400. For example, in one embodiment, pad 400 may be two sealed layers of material filled with temperature-sensing liquid crystals. Preferably, the layers may be sealed to ensure biocompatibility. Preferably, the layers may provide a time lag for heating the temperature-sensing elements 34 within pad 400. Such an arrangement may provide a surface that may more fully contact surface 64. The points of contact 70 on such an area may be nearly continuous.

Pad 400 may be placed against the surface 64 of the tissue to be ablated. Pad 400 may have a corresponding color scale (not shown). This color scale may indicate, for example, the current temperature, the maximum temperature achieved or that the tissue has reached a combination of temperature and time to ensure cell death.

During ablation, the user may view pad 400 to see a visual representation of the temperature of surface 64. For example, as shown in FIG. 5, pad 400 may be uniformly grey when first placed against surface 64. Then the pad 400 may turn darker grey when contacted against temperatures of about −20° C. Finally the pad 400 may turn black when contacted against temperatures of about −40° C. As seen in FIG. 5, pad 400 shows a representation 472 of lesion 72 that was created on surface 62. Using the grey/dark grey/black color scheme described above as an example, representation 472 indicates that lesion 72 has a temperature on the surface 64 of approximately −40° C. at the points that appear black in the representation. Lesion 72 has a temperature on surface 64 of approximately −20° C. at the points that appear dark grey in the representation. Lesion 72 has a temperature on surface 64 of greater than −20° C. at the portions that appear grey in the representation. A user may regard such a representation and determine that the dark grey portions and the grey portions of the lesion 72 need additional ablation. Additionally, a grid or other guide may be marked on pad 400 to aid the user in visualizing the lesion's placement.

The user may temporarily remove the pad to see whether the temperature of surface 64 is sufficient to achieve transmurality. When regarding the representation 472 described above, for example, the user may determine, based on the temperatures, that the dark grey portions and the grey portions of the lesion are not transmural. The user may then replace pad 400 and go back over the lesion with the ablation device 20 until the desired temperature is achieved. The desired temperature may correspond to transmurality as described above. Pad 400 may also be disposed after it is removed. A new pad may be placed under the lesion and the user may continue to ablate with device 20 and the new pad.

The embodiment of FIG. 5 may also include an electrode 423 which may serve as the return plate for energy transmitted through electrode 22. Electrode 423 may be, for example, a weeping electrode, a double wound coil electrodes, an electrode needles or any other suitable electrode. An electrically conductive element incorporated into pad 400 may serve as the electrode 423. Alternatively pad 400 may be electrically conductive and serve as electrode 423. Electrodes 22, 423 may act as anode and cathode to each other, completing a bipolar system. If electrodes 22 and 423 are close to each other, the electric current has less area to cross. This is beneficial because the current is less likely to cross into undesired areas (for example, tissue other than target tissue). Such a bipolar system is also known to create narrower and deeper lesions. Incorporation of electrode 423 into pad 400 may facilitate such a bipolar system.

Figure 6:
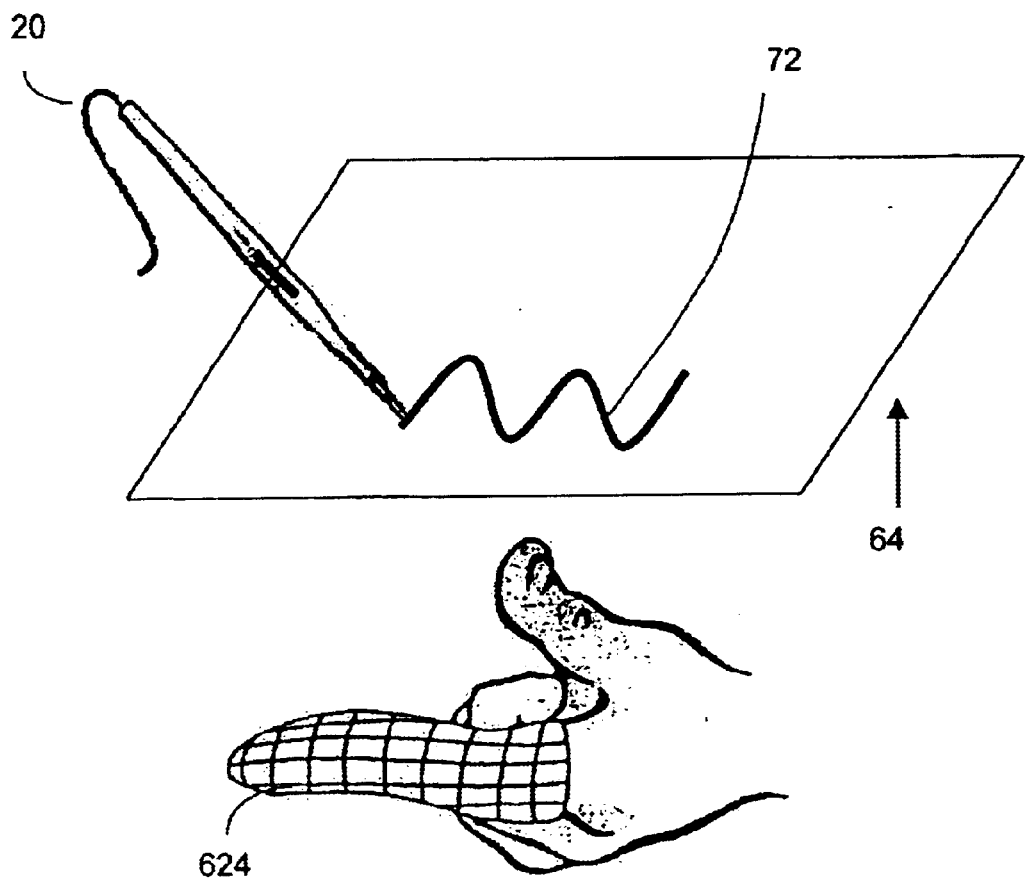
FIG. 6 illustrates another embodiment of a system for ablating tissue in accordance with the present invention.

As shown in FIG. 6, sensor 24 may be a finger pad 624. Sensor 24 may be mounted on a glove or a portion of a glove to form finger pad 624. Alternatively finger pad 624 may be formed of a material that may be used to cover a fingertip. Preferably finger pad 624 may be thermally insulated to protect the user.

During ablation, the user may view finger pad 624 to see a visual representation of the temperature of surface 64. For example, finger pad 624 may be uniformly blue when first placed against surface 64. Then the finger pad 624 may turn yellow when contacted against temperatures of about 30° C. Finally the finger pad 624 may turn red when contacted against temperatures of about 60° C. A grid may be marked on the pad 624 to aid the user in visualizing the lesion's placement.

The user may temporarily remove finger pad 624 from contact with surface 64. The user may then visually check the representation of the lesion displayed on finger pad 624. The representation may resemble, for example, whether the temperature of surface 64 is sufficient to achieve transmurality. If not, the user may replace finger pad 624 and go back over the lesion with the ablation device 20 until the desired temperature is achieved. Finger pad 624 may also be disposed after it is removed. A new pad may be placed under the lesion and the user may continue to ablate with device 20 and the new pad.

Figure 7:
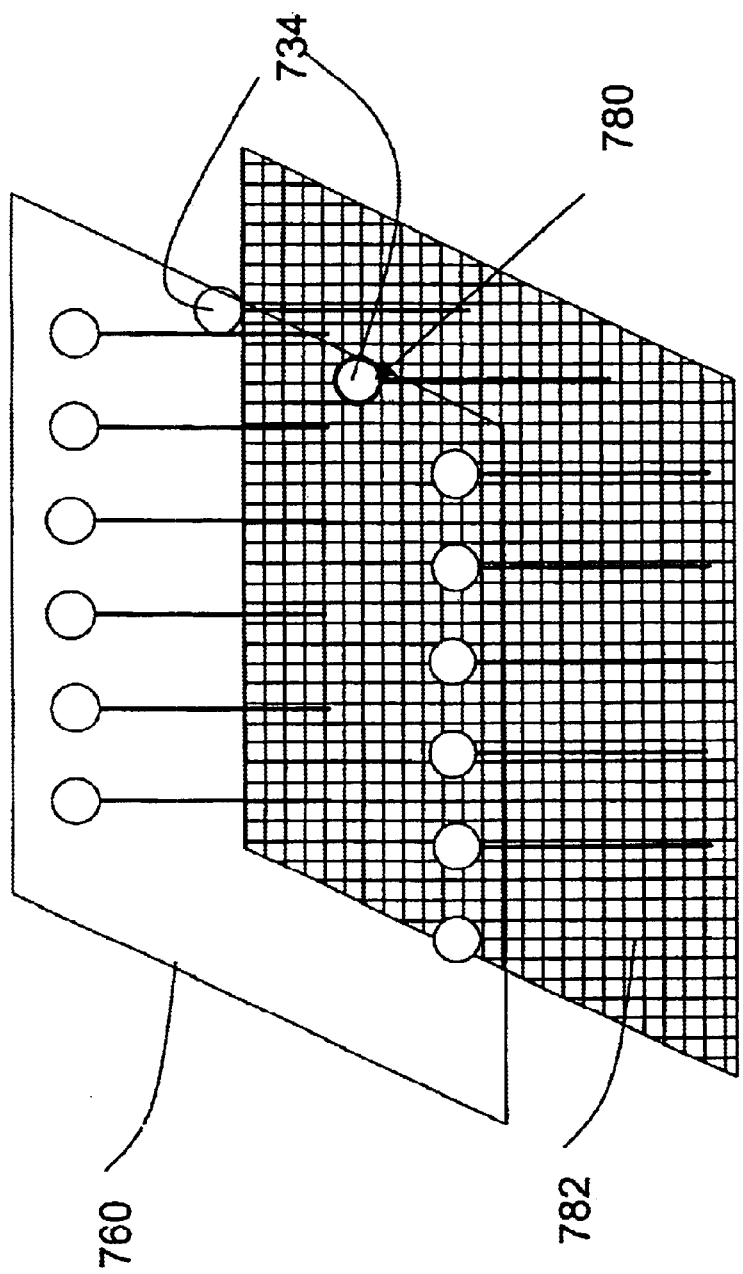
FIG. 7 illustrates another embodiment of a system for ablating tissue in accordance with the present invention.

FIG. 7 shows another embodiment of the temperature-sensing device of the present invention. In the embodiment shown in FIG. 7, pad 700 may incorporate temperature-sensing elements in a three-dimensional arrangement. Temperature-sensing elements 734 may be positioned so that they may be located within the tissue 760 itself. For example, a temperature-sensing element may be located at point 780 on the tip of a structure 782 for penetrating into the tissue. This structure may be any suitable element for positioning the elements 734 within the tissue, such as, for example, a needle. Temperature-sensing elements may be arranged on one or more of these structures 782. Temperature-sensing elements 734 may convey signals corresponding to the temperature of the tissue being ablated as described above.

As ablation occurs, it is sometimes desirable to irrigate the ablation site with irrigation fluid, which may be, for example, any suitable fluid such as saline or another conductive fluid. The irrigating fluid may cool the electrode 22 of ablation device 20 and may allow for greater lesion depth. Furthermore, continuous fluid flow may keep the ablation device surface temperature below the threshold for blood coagulation, which may also clog the device. Use of irrigating fluid may therefore reduce the need to remove a clogged ablation device for cleaning or replacement. The presence of an ionic fluid layer between electrode 22 and the tissue to be ablated may also ensure that an ionic fluid layer conforming to the tissue contours is created. In one preferred embodiment, saline solution is used. Alternatively, other energy-conducting liquids, such as Ringer's solution, ionic contrast, or even blood, may be used. Diagnostic or therapeutic agents, such as lidocaine, $CA^{++}$ blockers, ionic contrast, or gene therapy agents may also be delivered before, with or after the delivery of the irrigating fluid. Irrigation source 40 may be any suitable source of irrigation fluid such as, for example, a standard irrigation pump (not shown). This pump may also be connected to power source 30 or may have its own source of power. Preferably, device 20 also includes means for delivering irrigation to the ablation site from irrigation source 40. Such means may be, for example, fluid openings 46 which may be delivered to the electrode via, for example, fluid conduit 26.

System 10 may also include an indifferent electrode 23 which may serve as the return plate for energy transmitted through electrode 22. An electrically conductive element may be incorporated into sensor 24 or pad 400. Alternatively sensor 24 or pad 400 may be electrically conductive and serve as electrode 23. Alternatively, electrode 23 may be a separate electrically conductive element. Electrode 23 may be placed elsewhere on the patient's body than the ablation site. For example, electrode 23 may be placed on the patient's back or shoulder.

It is contemplated that the sensor for assessing transmurality of the present invention may be used in a variety of ablation systems such as those available from Medtronic, Inc., Minneapolis, Minn.

Figure 8:
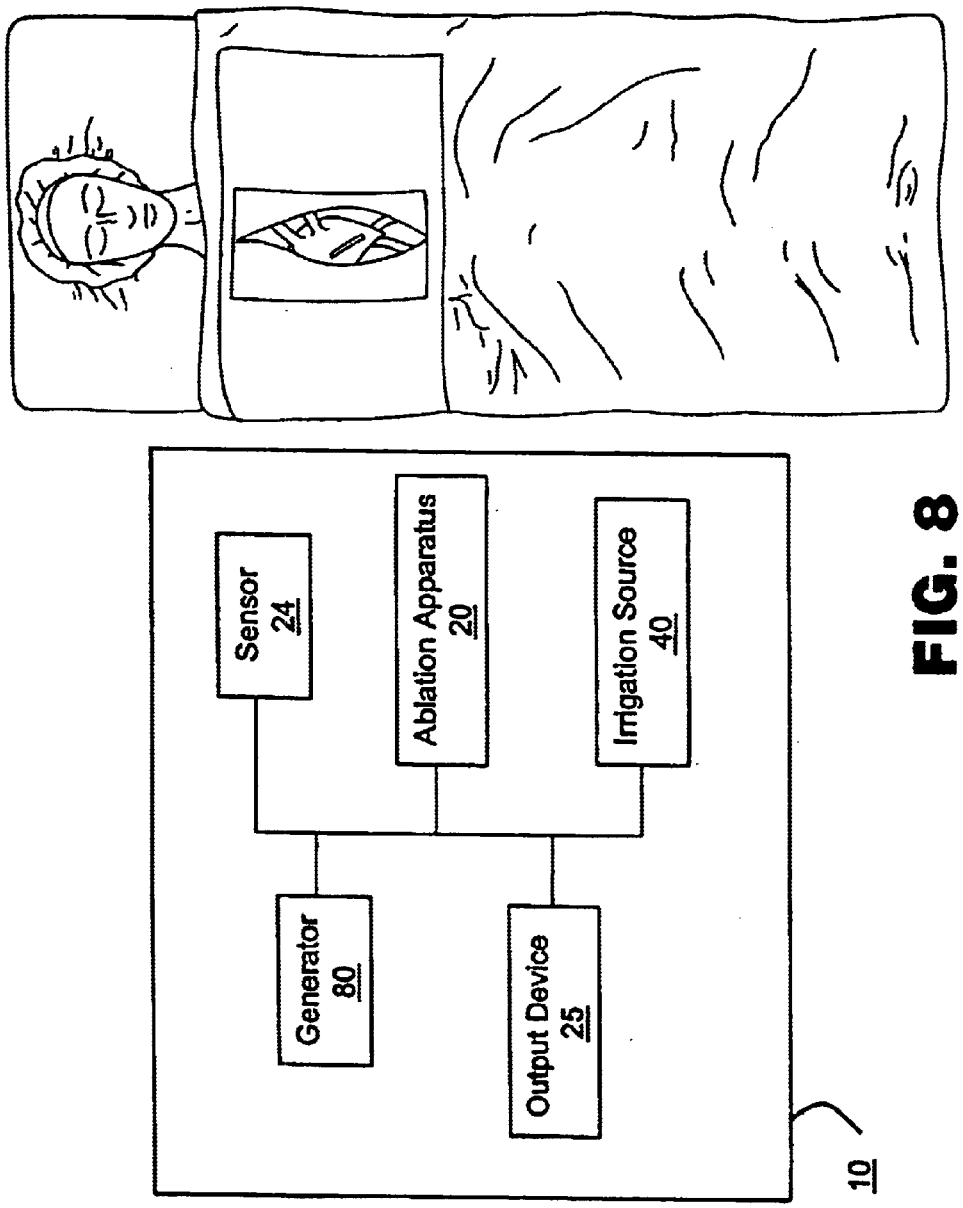
FIG. 8 illustrates another embodiment of a system for ablating tissue in accordance with the present invention.

FIG. 8 shows a schematic view of another embodiment of system 10 for ablating tissue in accordance with the present invention. In this embodiment, system 10 is shown to comprise ablation device 20, an output device 25, an irrigation source 40, a generator 80, and a sensor 24. As mentioned earlier, system 10 may also include an indifferent (non-ablating) electrode 23 (not shown in FIG. 6). As shown in FIG. 1, the indifferent electrode 23 may be placed elsewhere on the patient's body such as the back, thigh or shoulder or another site other than the ablation site.

Ablation device 20 may comprise one or more suction elements and a suction conduit that provides suction from a suction source. Ablation device 20 may also comprise a conduit that provides irrigation fluid from irrigation source 40. In addition, ablation device 20 may comprise a connector for connecting ablation device 20 to generator 80.

As discussed earlier, ablation device 20 and its components are preferably made of a biocompatible material. Biocompatible materials or biomaterials are usually designed and constructed to be placed in or onto tissue of a patient's body or to contact fluid of a patient's body. Ideally, a biomaterial will not induce undesirable reactions in the body such as blood clotting, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains in contact with tissues or fluids of the body.

Materials that are either biocompatible or may be modified to be biocompatible and may be used to make ablation device 20, sensor 24 and/or one or more of their components may include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, epoxies, human or animal protein or tissue such as bone, skin, teeth, collagen, laminin, elastin or fibrin, organic materials such as wood, cellulose, or compressed carbon, and other materials such as glass, and the like. Materials that are not considered biocompatible may be modified to become biocompatible by a number of methods well known in the art. For example, coating a material with a biocompatible coating may enhance the biocompatibility of that material.

One or more surfaces of ablation device 20, sensor 24 and/or their components may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized by a variety of methods well known in the art.

Ablation device 20 may comprise a surgeon controlled switch. For example, a switch may be incorporated in or on ablation device 20 or any other location easily and quickly accessed by the surgeon for regulation of ablation device 20 by the surgeon. The switch may be, for example, a hand switch, a foot switch, or a voice-activated switch comprising voice-recognition technologies.

A visual and/or audible signal used to alert a surgeon to the completion or resumption of ablation may be incorporated into ablation device 20. For example, a beeping tone or flashing light that increases in frequency as the ablation period ends or begins may be used.

Ablation device 20 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. It is contemplated that ablation device 20 may be used, for example, in open-chest surgery on a heart in which the sternum is split and the rib cage opened with a retractor. It is also contemplated that ablation device 20 may be used, for example, in closed-chest surgery on a heart in which the sternum is not split.

Figure 9:
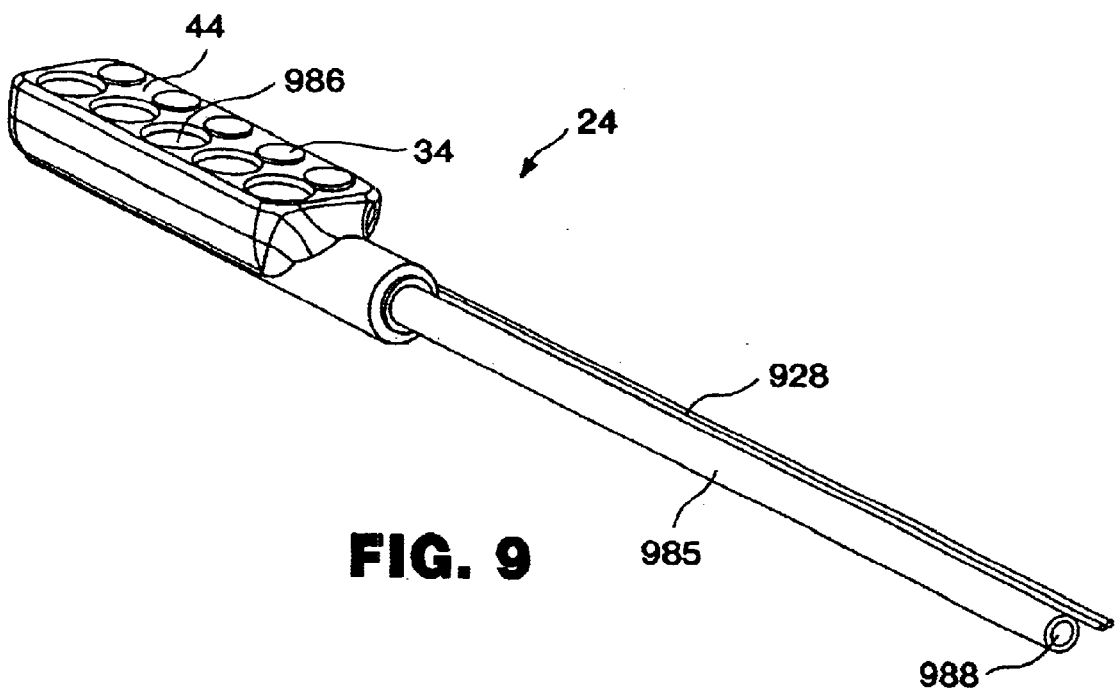
FIG. 9 illustrates another embodiment of a sensor device for sensing tissue temperature in accordance with the present invention.

System 10 may also include a suction source (not shown) for providing suction to ablation device 20 and/or sensor 24. Ablation device 20 may comprise one or more suction devices, elements, or ports to better anchor ablation device 20 to tissue. Suction may also be used to anchor sensor 24 to a surface of tissue. FIG. 9 shows an alternative embodiment of sensor 24 comprising a plurality of suction openings or ports 986 positioned along a tissue contact or support surface 44 comprising a plurality of temperature-sensing elements 34. Sensor 24 may comprise one or more suction elements, openings, orifices or ports positioned or integrated within or along a tissue contact or support surface. Suction openings of ablation device 20 and sensor device 24 may communicate suction through a tissue contact surface to the atmosphere. Sensor 24 may be powered by any suitable power source. For example, connection 928 may provide power to sensor 24 from power source 30, generator 80, output device 25, or processor 200.

Support surface 44 may be attached to a flexible or rigid hose or tubing for supplying suction from a suitable suction source to the target tissue surface through suction ports 986 of sensor 24. Support surface 44 may be attached to a maneuvering means for placing or positioning elements 34 against tissue. For example, sensor 24 may comprise shaft or handle 985 coupled to support surface 44. Handle 985 may comprise suction lumen 988 for communicating suction from a suitable suction source to the target tissue surface through suction ports 986 of sensor 24. Suction conduit or lumen 988 may be connected to least one suction port 986 containing a suction opening. Suction ports 986 may be arranged in any suitable fashion, such as a row or circle. In addition, the specific number of ports and their position may vary. Sensor 24 may be covered with a removable covering during insertion into a patient's body to prevent blood or tissue from clogging suction openings 986, although this is not necessary. Such coverings may include coverings of biocompatible material that would cover sensor 24. Alternatively, coverings may be placed over ports 986, such as, for example, mesh coverings or ribbed coverings.

Each suction port or opening 986 may have a suction aperture coupling port 986 with conduit 988. Suction aperture may be located in the center or at a position slightly off-center of suction port 986. Suction aperture may be any shape including circular. The suction ports 986 may also be any suitable shape, for example circular, oval, rectangular, or triangular.

Preferably, each suction aperture would have a smaller diameter than the area of suction port 986. This creates a high resistance pathway between suction port 986 and suction conduit 988. Because of this, loss of a tissue-to-port seal in one suction port (and thus loss of fixation of the suction port to the tissue) should not cause a precipitous pressure drop in the remainder of the suction ports.

Suction may be provided to ablation device 20 and/or sensor 24 by the standard suction available in the operating room. The suction source may be coupled to ablation device 20 and/or sensor 24 with a buffer flask. Suction may be provided at a negative pressure of between 200–600 mm Hg with 400 mm Hg preferred. Alternatively, suction may be provided via a manual or electric pump, a syringe, a suction or squeeze bulb or other suction or vacuum producing means, device or system. The suction source may comprise one or more vacuum regulators, valves, e.g., vacuum releasing valves, conduits, lines, tubes and/or hoses. The conduits, lines, tubes, or hoses may be flexible or rigid. For example, a flexible suction line may be used to communicate suction to ablation device 20 and/or sensor 24, thereby allowing ablation device 20 and/or sensor 24 to be easily manipulated by a surgeon. Another method that would allow the surgeon to easily manipulate ablation device 20 and/or sensor 24 includes incorporation of a suction source into ablation device 20 and/or sensor 24. For example, a small battery operated vacuum pump may be incorporated into ablation device 20 and/or sensor 24.

The suction source may be slaved to ablation device 20, output device 25, irrigation source 40, generator 80 and/or sensor 24. For example, the suction source may be designed to automatically stop suction when ablation is stopped and to start suction when ablation is began. The suction source may include a visual and/or audible signal used to alert a surgeon to any change in suction. For example, a beeping tone or flashing light may be used to alert the surgeon when suction is present.

Figure 10:
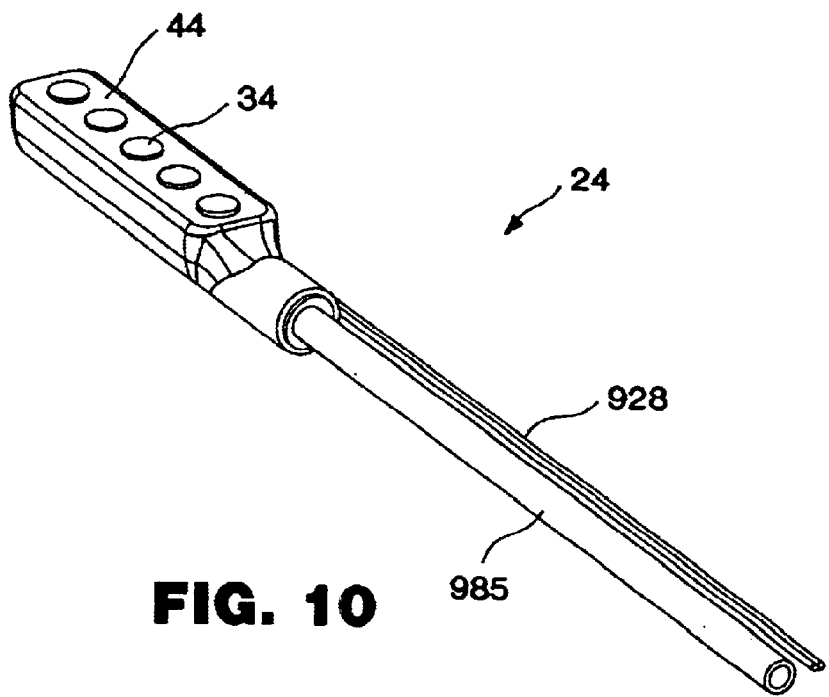
FIG. 10 illustrates another embodiment of a sensor device for sensing for tissue temperature in accordance with the present invention.

FIG. 10 shows an alternative embodiment of sensor 24 comprising a plurality of temperature-sensing elements 34 aligned in a row on tissue contact or support surface 44. Tissue contact surface 44 may be attached to shaft or handle 985. Handle 985 may be rigid or flexible. Handle 985 may comprise one or more hinges or joints (not shown) for maneuvering and placing elements 34 against tissue. The hinges or joints of handle 985 may be actuated remotely, for example, from outside a patient's body. Handle 985 may be malleable or shapeable. Connection 928 may provide power to sensor 24 from power source 30, generator 80, output device 25, or processor 200.

Sensor 24 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. It is contemplated that sensor 24 may be used, for example, in open-chest surgery on a heart in which the sternum is split and the rib cage opened with a retractor. It is also contemplated that sensor 24 may be used, for example, in closed-chest surgery on a heart in which the sternum is not split.

Sensor 24 may include or be operatively coupled with a surgeon-controlled switch. For example, a switch may be incorporated in or on sensor 24 or any other location easily and quickly accessed by the surgeon for regulation of sensor 24 by the surgeon. The switch may be, for example, a hand switch, a foot switch, or a voice-activated switch comprising voice-recognition technologies.

Sensor 24 may include, or may be coupled with a device that generates, a visual and/or audible signal used to alert a surgeon to any change in tissue temperature. For example, a beeping tone or flashing light may be used to alert the surgeon that a change has occurred in tissue temperature.

Output device 25 may receive and preferably interpret the signal from sensor 24. The signal from sensor 24 may preferably be amplified by a suitable amplifier 220 before reaching output device 25 comprising processor 200. The amplifier may be incorporated into output device 25. Alternatively, the amplifier may be incorporated into sensor 24, ablation device 20 or generator 80. Alternatively, the amplifier may be a separate device. Output device 25 may be a device separate from ablation device 20, sensor 24, power source 30, irrigation source 40, or generator 80. Output device 25 may be incorporated into ablation device 20, sensor 24, power source 30, irrigation source 40, or generator 80. Output device 25 may control the power level from the power source 30 or generator 80. For example, a signal of a first intensity from sensor 24 may indicate that the power level from power source 30 should be lowered; a signal of a different intensity may indicate that the power source 30 should be turned off. Preferably, output device 25 may be configured so that it may automatically raise or lower the power from source 30 appropriately. Alternatively, the control of power source 30 based on output from output device 25 may be manual.

Output device 25 may also be a visual display that indicates to the user that ablation energy should be halted. Such a display may be, for example, an indicator on a LCD or CRT monitor 210. By software control, the user may choose to display the information in a number of ways. The monitor 210 may show the current temperature of each point of contact 70. The monitor 210 may also lock and display the maximum temperature achieved at each point of contact 70. The monitor 210 may also indicate when each point of contact has reached an appropriate combination of temperature and time to ensure cell death. One such appropriate combination may be 60° C. for 5 seconds. Another combination may be 55° C. for 20 seconds. Another combination may be 50° C. for 15 seconds. Temperature information may be displayed to the user in any other suitable manner, such as for example, displaying a virtual representation of sensor 24 and ablation lesion 72 on the monitor 210.

Alternatively, the monitor may display the voltage corresponding to the signal emitted from sensor 24. This signal corresponds in turn to the intensity of the temperature at the tissue site. Therefore a voltage level of 2 would indicate that the tissue was hotter than when the voltage level was 1. In this example, a user would monitor the voltage level and, if it exceeded a certain value, would turn off or adjust the power source 30.

The display of device 25 may alternatively be located on sensor 24 or ablation device 20. An indicator, such as an LED light, may be permanently or removably incorporated into sensor 24 or ablation device 20. The indicator may receive a signal from sensor 24 indicating that the tissue had reached an appropriate temperature. In response, the indicator may turn on, change color, grow brighter or change in any suitable manner to indicate that the flow of power from source 30 should be modified or halted. The indicator may also be located on power source 30, on generator 80, on irrigation source 40, or may be located on another location visible to the user.

Alternatively, output device 25 may be an audio device that indicates to the user that ablation energy should be halted. Such an audio device may be, for example, a speaker that broadcasts a sound (for example, a beep) that increases in intensity, frequency or tone as the temperature sensed by sensor 24 increases. The user may adjust, for example, turn down or turn off power source 30 when the sound emitted reaches a given volume or level. In another embodiment, the audio device may also give an audible signal (such as the message "turn off power source") when the temperature sensed by sensor 24 reaches a certain level. Such an audio device may be located on the sensor 24 or ablation apparatus 20, on power source 30, on generator 80, or on irrigation source 40. The audio device may also be a separate device.

Figure 11:
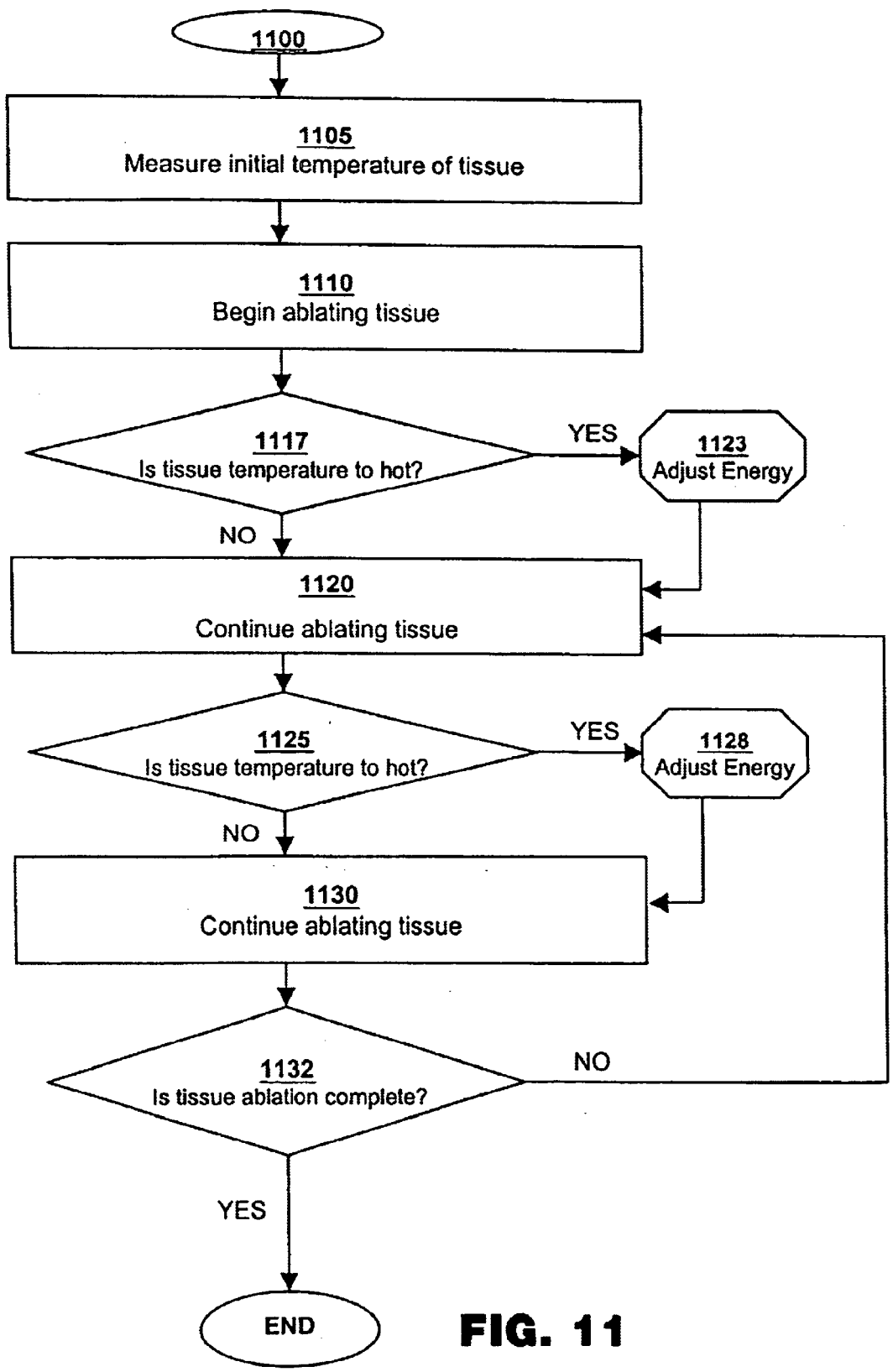
FIG. 11 shows a flow diagram of one embodiment of the present invention.

FIG. 11 shows a flow diagram of one embodiment of the present invention. The patient is prepared for an ablation procedure at 1100. Once the patient is prepared, the initial state of tissue temperature is measured (Block 1105). The initial state of tissue temperature is then used as a gauge to compare with the state of tissue temperature during the procedure. At this point, ablation of the target tissue is begun (Block 1110). Tissue temperature is then monitored (Blocks 1117 and 1125). If the tissue temperature becomes to hot, the energy supplied to ablation apparatus 20 is modified or adjusted (Blocks 1123 and 1128).

Irrigation source 40, as discussed above, may be any suitable source of irrigation fluid. Irrigation source 40 may include a manual or electric pump, an infusion pump, a syringe pump, a syringe, a pressurized reservoir or bag, a squeeze bulb or other fluid moving means, device or system. For example, a pump may be connected to power source 30 or it may have its own source of power. Irrigation source 40 may be powered by AC current, DC current, or it may be battery powered either by a disposable or re-chargeable battery. Irrigation source 40 may comprise one or more fluid regulators, e.g., to control fluid flow rate, valves, fluid reservoirs, conduits, lines, tubes and/or hoses. The conduits, lines, tubes, or hoses may be flexible or rigid. For example, a flexible line may be used to communicate fluid to ablation device 20, thereby allowing ablation device 20 to be easily manipulated by a surgeon. Fluid reservoirs, for example, may be an IV bag or bottle. It is preferred that the irrigation fluid be sterile.

Irrigation source 40 may be incorporated into ablation device 20, thereby delivering irrigation fluid at the ablation site. Irrigation source 40 may be slaved to ablation device 20, output device 25, generator 80 and/or sensor 24. For example, irrigation source 40 may be designed to automatically stop or start the delivery of irrigation fluid during ablation of tissue. Irrigation source 40 may be slaved to a robotic system or a robotic system may be slaved to irrigation source 40.

Irrigation source 40 may comprise a surgeon-controlled switch. For example, a switch may be incorporated in or on irrigation source 40 or any other location easily and quickly accessed by the surgeon for regulation of irrigation fluid delivery by the surgeon. The switch may be, for example, a hand switch, a foot switch, or a voice-activated switch comprising voice-recognition technologies.

Irrigation source 40 may include a visual and/or audible signal used to alert a surgeon to any change in the delivery of irrigation fluid. For example, a beeping tone or flashing light may be used to alert the surgeon that a change has occurred in the delivery of irrigation fluid.

As discussed earlier, an irrigation fluid may include saline, e.g., normal, hypotonic or hypertonic saline, Ringer's solution, ionic contrast, blood, or other energy-conducting liquids. An ionic irrigation fluid electrically couples the one or more electrodes of ablation device 20 to the tissue to be ablated thereby lowering the impedance at the ablation site. An ionic irrigating fluid may create a larger effective electrode surface. An irrigating fluid may cool the surface of the tissue thereby preventing the over heating or cooking of tissue which can cause popping, desiccation, and charring of tissue. A hypotonic irrigating fluid may be used to electrically insulate a region of tissue thereby preventing ablation of tissue by an electrical means.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered before, with or after the delivery of the irrigating fluid. Biological agents may be found in nature (naturally occurring) or may be chemically synthesized. Cells and cell components, e.g., mammalian cells, may be delivered before, with or after the delivery of the irrigating fluid.

Generator 80 may comprise a control unit and power source 30. Ablation device 20 may be permanently or removably attached to a source of energy such as electrical, radiofrequency (RF), laser, thermal, microwave or ultrasound or any other appropriate type of energy that may be used to ablate tissue. Generator 80 may be powered by AC current, DC current or it may be battery powered either by a disposable or re-chargeable battery. Generator 80 may be used to coordinate the various elements of system 10. For example, generator 80 may be configured to synchronize activation and deactivation of irrigation source 40 with ablation.

Generator 80 may incorporate a controller as described above or any suitable processor. For example, the processor may process sensed information from sensor 24. The controller may store and/or process such information before, during and/or after an ablation procedure. For example, the patient's tissue temperature may be sensed, stored and processed prior to and during the ablation procedure.

Generator 80 may be used to control the power levels of ablation device 20. Generator 80 may also gather and process information from sensor 24. This information may be used to adjust power levels and ablation times. Generator 80 may incorporate one or more switches to facilitate regulation of the various system components by the surgeon. One example of such a switch is a foot pedal. The switch may also be, for example, a hand switch, or a voice-activated switch comprising voice-recognition technologies. The switch may be incorporated in or on one of the surgeon's instruments, such as surgical site retractor, e.g., a sternal or rib retractor, or ablation device 20, or any other location easily and quickly accessed by the surgeon. Generator 80 may also include a display. Generator 80 may also include other means of indicating the status of various components to the surgeon such as a numerical display, gauges, a monitor display or audio feedback.

Generator 80 may also incorporate a cardiac stimulator and/or cardiac monitor. For example, electrodes used to stimulate or monitor the heart may or may not be incorporated into ablation device 20 and/or sensor 24. Generator 80 may comprise a surgeon-controlled switch for cardiac stimulation or monitoring, as discussed earlier. For example, a switch may be incorporated in or on generator 80 or any other location easily and quickly accessed by the surgeon for regulation of generator 80 by the surgeon. The switch may be, for example, a hand switch, a foot switch, or a voice-activated switch comprising voice-recognition technologies.

A visual and/or audible signal used to alert a surgeon to the completion or resumption of ablation, suction, sensing, monitoring, stimulation and/or delivery of irrigation fluid, drugs and/or cells may be incorporated into generator 80. For example, a beeping tone or flashing light that increases in frequency as the ablation period ends or begins may be used.

System 10 may comprise one or more additional sensors besides sensor 24. For example, ablation device 20 may comprise one or more temperature-sensitive elements, such as a thermocouple, to allow a surgeon to monitor temperature changes of ablation device 20. Alternatively, system 10 or ablation device 20 may comprise one or more sensors to sense and/or monitor voltage, amperage, wattage and/or impedance.

Alternatively, system 10, ablation device 20, or sensor 24 may comprise one or more blood gas sensors for measuring the concentration or saturation of a gas in the blood stream. For example, system 10, ablation device 20, or sensor 24 may comprise a sensor for measuring the concentration or saturation of oxygen or carbon dioxide in the blood. Alternatively, system 10, ablation device 20, or sensor 24 may comprise one or more suitable sensors for measuring blood pressure or flow, for example a Doppler ultrasound sensor system, or a sensor for measuring hematocrit (HCT) levels.

Alternatively, system 10, ablation device 20, or sensor 24 may comprise one or more biosensors, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

System 10, ablation device 20, or sensor 24 may comprise one or more sensors based on potentiometric technology or fiber optic technology. For example, the sensor may comprise a potentiometric or fiber optic transducer. An optical sensor may be based on either an absorbance or fluorescence measurement and may include an UV, a visible or an IR light source.

System 10, ablation device 20, or sensor 24 may comprise one or more sensors used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, impedance, temperature, pressure, components of metabolic processes, chemical concentrations, for example, the absence or presence of specific peptides, proteins, enzymes, gases, ions, etc.

System 10, ablation device 20, or sensor 24 may comprise one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, sound wave sensors; magnetic sensors; UV light sensors; visible light sensors; IR light sensors; radiation sensors; flow sensors; temperature sensors; vacuum sensors; or any other appropriate or suitable sensor.

Sensors may be incorporated into ablation device 20 or they may be placed or used at a location differing from the location of ablation device 20. For example, sensors may be placed in contact with the inside surface of a patient's heart while ablation device 20 is placed or used on the outside surface of the patient's heart.

Ablation device 20, irrigation source 40 and/or generator 80 may be slaved to one or more sensors. For example, ablation device 20 and/or generator 80 may be designed to automatically stop ablation if a sensor measures a predetermined sensor value, e.g., a particular temperature value. In one embodiment of the invention, if a sensor of the present invention indicates that ablated tissue has reached a particular temperature, ablation is stopped automatically, thereby preventing charring of the tissue. Suction may also be slaved to one or more sensors.

One or more sensors of the present invention may include a visual and/or audible signal used to alert a surgeon to any change in the one or more characteristics the sensor is monitoring. For example, a beeping tone or flashing light that increases in frequency as tissue temperature rises may be used to alert the surgeon.

Ablation device 20, output device 25, irrigation source 40, generator 80, and/or sensor 24 may be slaved to a robotic system or a robotic system may be slaved to ablation device 20, output device 25, irrigation source 40, generator 80, and/or sensor 24. Additional sensors and/or a suction source may also be slaved to a robotic system or a robotic system may be slaved to the additional sensors and/or the suction source. Computer- and voice-controlled robotic systems that position and maneuver endoscopes and/or other surgical instruments for performing microsurgical procedures through small incisions may be used by the surgeon to perform precise and delicate maneuvers. These robotic systems may allow the surgeon to perform a variety of microsurgical procedures including tissue ablation. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

One or more of a variety of pharmacological agents or drugs may be delivered or administered to an ablation patient, for a variety of functions and purposes as described below, prior to an ablation procedure, intermittently during an ablation procedure, continuously during an ablation procedure and/or following an ablation procedure. For example, one or more of a variety of pharmacological agents or drugs, as discussed below, may be delivered before, with or after the delivery of the irrigating fluid, as discussed earlier.

Drugs, drug formulations or compositions suitable for administration to an ablation patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, system 10 may include a drug delivery device (not shown). The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as nerve stimulation electrodes or as cardiac stimulation electrodes.

A drug delivery device may be incorporated into ablation device 20, thereby delivering drugs at or adjacent the ablation site or the drug delivery device may be placed or used at a location differing from the location of ablation device 20. For example, a drug delivery device may be placed in contact with the inside surface of a patient's heart while ablation device 20 is placed or used on the outside surface of the patient's heart.

The drug delivery device may be slaved to ablation device 20, output device 25, generator 80 and/or sensor 24. For example, a drug delivery device may be designed to automatically stop or start the delivery of drugs during ablation of tissue. The drug delivery device may be slaved to a robotic system or a robotic system may be slaved to the drug delivery device.

The drug delivery device may comprise a surgeon controlled switch. For example, a switch may be incorporated in or on the drug delivery device or any other location easily and quickly accessed by the surgeon for regulation of drug delivery by the surgeon. The switch may be, for example, a hand switch, a foot switch, or a voice-activated switch comprising voice-recognition technologies.

The drug delivery device may include a visual and/or audible signal used to alert a surgeon to any change in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or -adrenergic blocking agents are also known as beta-blockers or -blockers and as class 11 antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

One or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered or administered to an ablation patient prior to an ablation procedure, intermittently during an ablation procedure, continuously during an ablation procedure and/or following an ablation procedure. Biological agents may be found in nature (naturally occurring) or may be chemically synthesized.

The ablation procedure may be non-invasive, minimally invasive and/or invasive. The ablation procedure may entail a port-access approach, a partially or totally endoscopic approach, a sternotomy approach or a thoracotomy approach. The ablation procedure may include the use of various mechanical stabilization devices or techniques as well as various robotic or imaging systems. For example, mechanical stabilization and manipulation devices are described in U.S. Pat. Nos. 5,836,311; 5,927,284 and 6,015,378, and co-assigned U.S. patent applications Ser. No. 09/396,047, filed Sep. 15, 1999, Ser. No. 09/559,785, filed Apr. 27, 2000, and Ser. No. 09/678,203, filed Oct. 2, 2000; and European Patent Publication No. EP 0 993 806. These patents and applications are assigned to Medtronic, Inc. and are incorporated herein by reference.

In one method of the present invention, the heart may be temporarily slowed or intermittently stopped for short periods of time to permit the surgeon to accomplish a required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers", Dec. 21, 1999, to Hill and Junkman. This patent is assigned to Medtronic, Inc. and is incorporated herein by reference.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of ablating organic tissue comprising the steps of:

providing a temperature-sensing pad operatively adapted to sense a temperature of the tissue and an output device in communication with the pad, the output device operatively adapted to display a representation of a lesion found on a back side of the tissue;

positioning the pad against a back side of the tissue;

ablating the tissue with an ablation apparatus against a front side of the tissue;

sensing the temperature changes of the ablated tissue with the pad; and ablating the tissue in accordance with the temperature changes.

2. The method of claim 1 further comprising:

viewing the representation of the lesion; and correlating the temperature changes of the ablated tissue with the representation of the lesion.

* * * * *